United States Patent [19]

Mosher et al.

[11] Patent Number: 5,114,413
[45] Date of Patent: May 19, 1992

[54] METHODS TO MAKE AND USE PROTEINACEOUS MATERIAL PRESENT IN KININ-FREE HIGH MOLECULAR WEIGHT KININOGEN

[75] Inventors: Deane F. Mosher; Shinji Asakura, both of Madison, Wis.

[73] Assignee: Wisconsin Alumni Research Foundation, Madison, Wis.

[21] Appl. No.: 544,133

[22] Filed: Jun. 8, 1990

[51] Int. Cl.$^5$ ................ A61M 5/32; A61M 25/00
[52] U.S. Cl. .................... 604/266; 514/802; 435/2; 623/1
[58] Field of Search ................ 604/266–269, 604/264; 623/1, 11, 12.66; 514/803; 435/2

[56] References Cited

U.S. PATENT DOCUMENTS

| 4,999,210 | 3/1991 | Solomon et al. | 427/2 |
| 5,019,393 | 5/1991 | Ito et al. | 424/423 |
| 5,047,020 | 9/1991 | Hsu | 604/266 |
| 5,053,048 | 10/1991 | Pinchuk | 623/1 |

FOREIGN PATENT DOCUMENTS

| 0039983 | 3/1979 | Japan | 604/266 |
| 0047799 | 4/1979 | Japan | 604/266 |
| 0135494 | 10/1979 | Japan | 604/266 |
| 0118763 | 7/1983 | Japan | 604/266 |

OTHER PUBLICATIONS

D. Kerbiriou et al., 254 J. Bio. Chem. 12020–12027 (1979).
L. Vroman et al., 55 Blood 156–159 (1980).
A. Schmaier et al., 33 Throm. Res. 51–67 (1983).
C. Scott et al., 73 J. Clin. Invest. 954–962 (1984).
Y. Takagaki et al., 260 J. Bio. Chem. 8601–8609 (1985).
J. Tait et al., 261 J. Bio. Chem. 15396–15401 (1986).
K. Fujikawa et al., 12 Biochem. 4938–4945 (1973).
K. Fujikawa et al., 19 Biochem. 1322–1330 (1980).

Primary Examiner—C. Fred Rosenbaum
Assistant Examiner—Mark O. Polutta
Attorney, Agent, or Firm—Quarles & Brady

[57] ABSTRACT

Disclosed herein are methods for using a proteinaceous material present in kinin free high molecular weight kininogen to treat surfaces to prevent or minimize adhesion by blood components and/or animal cells. For example, in medical applications, one can treat plastic tubes or other conduits that carry blood to reduce the tendency of the blood to block the conduit. Also disclosed is an improved method of purifying kinin free high molecular weight kininogen.

7 Claims, No Drawings

METHODS TO MAKE AND USE PROTEINACEOUS MATERIAL PRESENT IN KININ-FREE HIGH MOLECULAR WEIGHT KININOGEN

This invention was made with United States government support awarded by the National Institute of Health (NIH), Grant #PO1 HL29586. The United States Government has certain rights in this invention.

TECHNICAL FIELD

The invention relates generally to a plasma protein known as high molecular weight ("HMW") kininogen. More particularly, it relates to use of a proteinaceous material present in kinin-free HMW kininogen to reduce surface adhesion on surfaces exposed to blood components and/or animal cells, and to improved methods for purifying kinin-free HMW kininogen.

BACKGROUND ART

High molecular weight ("HMW") kininogen and low molecular weight ("LMW") kininogen are known kininogens in blood plasma. Both of these kininogens carry a kinin protein moiety in their polypeptide chain. This region is in turn bridged by a disulfide bond so as to form a looped structure. Upon liberation of the kinin protein (through the operation of an enzyme known as kallikrein) dimer variants of these compounds are formed. In the HMW variant, liberation of kinin results in a disulfide bonded dimer of an amino-terminal H-chain and a carboxyl L-chain. See generally Y. Takagaki et al. 260 J. Biol. Chem. 8601–8609 (1985).

The H-chains of HMW and LMW kininogens are identical. However, the L-chains are different. The L-chain of the HMW kininogen is larger than the L-chain of the LMW kininogen, and is known to contain a region rich in histidine, a region rich in basic residues, and a region rich in acidic acid residues. It is also known that two other plasma proteins (pre-kallikrein and blood coagulation Factor XI) bind to HMW kininogen via the acidic region in the L-chain (J. Tait et al., 261 J. Biol. Chem. 15396–15401 (1986)); and that binding of HMW kininogen to negatively charged surfaces is enhanced by cleavage to form the two chain kinin free form (C. Scott et al., 73 J. Clin. Invest. 954–962 (1984)).

The mechanism of cleavage is thought to involve binding of HMW kininogen and pre-kallikrein (and HMW kininogen Factor XI complexes) to surfaces alongside blood coagulation Factor XII. This is referred to as "contact activation". Reciprocal activation of the surface generates the enzyme kallikrein, which then in turn cleaves the HMW kininogen to yield a polypeptide previously named "kinin-free HMW kininogen" (herein referred to as "passifin"). See also L. Vroman et al., 55 Blood 156–159 (1980) and A. Schmaier et al., 33 Thromb. Res. 51–67 (1983).

While considerable research has been run on the function and structure of kinin-free HMW kininogen, there has to date been no suggestion in the art that a conduit or other surface normally exposed to blood and/or animal cells could first be exposed to an exogenous (from outside the host) supply of a proteinaceous material present in kinin-free HMW kininogen to reduce the tendency of the blood to block the conduit or surface.

SUMMARY OF THE INVENTION

In one aspect, the invention provides a method for reducing the tendency of animal cells and/or blood components to adhere to a surface. The method involves exposing the surface to an exogenously supplied proteinaceous material present in passifin. The material preferably has at least 50 amino acids, of which at least 5 are histidine. The best currently known material for this purpose is the entire passifin polypeptide. For example, one can coat the interior of a plastic (or other material) tube used to transport blood into and/or out of the body with passifin. This will reduce clogging problems.

In another aspect, the invention provides a means to separate out passifin from histidine rich glycoprotein and/or antithrombin III. One uses passifin's binding affinity to a sulfated polysaccharide for this purpose. Preferably, the sulfated polysaccharide is heparin and during the separating step the heparin has been immobilized on a column (e.g. heparin-sepharose; heparin agarose). The mixture can be eluted through the column using a linear salt gradient. To obtain even higher yields, the mixture can be formed by exposing animal plasma to dextran sulfate or other substances that enhance contact activation (e.g. kaolin).

In yet another aspect, surfaces treated with such proteinaceous materials are provided.

It is expected that only a portion of passifin will be needed to reduce the tendency of blood components and/or animal cells to adhere to surfaces in some environments. In this regard, the histidine rich part of the L-chain of passifin appears to be required.

It will also be appreciated that heparin (and perhaps other sulfated polysaccharides such as dextran sulfate or fucoidan) has an ability to distinguish passifin vis a vis certain other contaminants found in plasma. This permits efficient purification of passifin.

The objects of the present invention therefore include providing methods of the above kind to pretreat surfaces in order to reduce the tendency of blood components and/or animal cells to stick to them, and methods to more efficiently purify passifin. Another object is to provide surfaces (e.g. conduits) that have been treated in this manner. Still other objects and advantages of the present invention will be apparent from the description which follows. The following description is merely of the preferred embodiments. The claims should be looked to understand the full scope of the invention.

BEST MODE FOR CARRYING OUT THE INVENTION

In order to obtain kinin free HMW kininogen ("passifin") one previously followed the procedure of D. Kerbirious et al., 254 J. Biol. Chem. 12020-14 12027 (1979). This procedure can be modified by the use of dextran sulfate to improve production yields. See K. Kurachi et. al., 19 Biochem. 1322–1330 (1980).

This method can be improved even further as follows. One begins with fresh frozen plasma. For purposes of precipitating out vitamin K dependent factors, one adds $BaCl_2$ to a final concentration of 90 mM at 4° C. and stirs for one hour. After centrifuging for 20 minutes at 500 g, the supernatant is saved. One then adds dextran sulfate to a final concentration of 0.1% and stirs for 30 minutes at 4° C.

One then precipitates out a mixture of proteins (including passifin) with 20–60% saturated ammonium sulfate, and takes the precipitate and runs extensive dialysis against a slightly acidic buffer with high salt concentration (e.g. 20 mM phosphate buffer, pH 6.3 and 0.47 M NaCl).

In accordance with the present invention, one then separates out passifin from the mixture on a column of immobilized heparin agarose prepared in accordance with K. Fujikawa et al., 12 Biochem. 4938–4945 (1973). The column is developed with a linear salt gradient. Surprisingly, it has been learned that passifin binds to the column and elutes in linear salt gradients (0.4–1.0 M) prior to elution of histidine rich glycoprotein and antithrombin III. The desired fraction can be detected by immunoassays with anti-HMW kininogen antibodies, distinctive patterns in SDS PAGE, or anti-adhesive activity as described below.

EXPERIMENT 1

Polystyrene cell culture plates were precoated with vitronectin (a plasma protein which supports cell adhesion to the plates) (and/or a passifin/vitronectin mixture). Three types of tumor cells and one endothelial cell type were then spread on the plates. Cells did not spread on plates having the mixture, whereas they did spread on plates coated only with vitronectin.

EXPERIMENT 2

Similar experiments were tried by coating plates with fibrinogen (another blood plasma protein that supports adhesion) (and/or fibrinogen/passifin mixtures), using blood platelets or mononuclear blood cells, and/or using endothelial cells. Similar results were obtained.

EXPERIMENT 3

Prior to placement in an arteriovenous shunt, segments of polyethylene tubing were coated with one of the following:
a. nothing
b. vitronectin
c. fibrinogen (100 μg/ml)
d. passifin
e. vitronectin and passifin
f. fibrinogen (100 μg/ml) and passifin (30 μg/ml)

The surfaces coated with passifin, or a combination of passifin/vitronectin accumulated significantly less platelets than the uncoated surface, or the surface coated with fibrinogen.

EXPERIMENT 4

A very preliminary test was performed on a canine coronary artery using a mechanically damaged artery that had been filled with passifin for a very short period of time. The results under these conditions did not show a reduction in thrombogenic activity. However, additional tests will be made with respect to canine (and human) arteries (and other blood conduits).

SEQUENCE INFORMATION

Seq. No. 1 described hereafter shows the previously known amino acid sequence of HMW kininogen. The Arg-Pro- . . . -Arg sequence at 363-371 is the sequence that is cleaved out to form passifin. The disulfide bond is between the Cys at 10 and the Cys at 596. The light chain starts at 372 and runs to the end. The heavy chain starts at 1 and runs to 362. The histidine rich region is between 372 and 553 (e.g. 407–505).

It will be appreciated that the above description provides a description of the preferred embodiments. Other embodiments of the invention are also intending to be within the spirit and scope of the claims. For example, recombinant clones may be able to express just portions of the proteinaceous material of passifin (e.g. the histidine rich section). Also, while circular HMW kininogen itself does not have the property of interest, cleaved dimer forms having the histidine rich section (and even also the kinin sequence) may work. Thus, many modifications to the invention are intended to be included within scope of the claims.

SEQUENCE LISTING

1. GENERAL INFORMATION
   APPLICANTS: Mosher, Deane F.; Asakura, Shinji (n.m.i.)
   (ii) TITLE OF INVENTION: Methods To Make And Use Proteinaceous Material Present In Kinin-Free High Molecular Weight Kininogen
   (iii) NUMBER OF SEQUENCES: 1
   (iv) CORRESPONDENCE ADDRESS:
   (A) ADDRESSEE: Carl R. Schwartz c/o Quarles & Brady
   (B) STREET: 411 East Wisconsin Avenue
   (C) CITY: Milwaukee
   (D) STATE: Wisconsin
   (E) COUNTRY: U.S.A.
   (F) ZIP: 53202
   (v) COMPUTER READABLE FORM:
   (A) MEDIUM TYPE: Diskette 5.25 Inch, 1.2 Mb Storage
   (B) COMPUTER: Compaq Deskpro 280/ IBM Compatible
   (C) OPERATING SYSTEM: MS-DOS Version 3.20
   (D) SOFTWARE: Microsoft Word Version 5.0A, "Text Only"
   (vi) CURRENT APPLICATION DATA
   (A) APPLICATION NUMBER: 07/544,133
   (B) FILING DATE: 8 Jun. 1990
   (vii) SEQUENCE CHARACTERISTICS
   (A) LENGTH: 626
   (B) TYPE: amino acid chain
   (C) STRANDEDNESS: single with disulfide link
   (D) TOPOLOGY: circular due to disulfide link Sequence Description: Seq Id No: 1:

5'--
| CAG | GAA | UCA | CAG | UCC | GAG | GAA | AUU | GAC | UGC | AAU | GAC | AAG | 39 |
| Gln | Glu | Ser | Gln | Ser | Glu | Glu | Ile | Asp | <u>Cys</u> | Asn | Asp | Lys | |
| 1 | | | | 5 | | | | | 10 | | | | |

| GAU | UUA | UUU | AAA | GCU | GUG | GAU | GCU | GCU | CUG | AAG | AAA | UAU | 78 |
| Asp | Leu | Phe | Lys | Ala | Val | Asp | Ala | Ala | Leu | Lys | Lys | Tyr | |
| | 15 | | | | | 20 | | | | | 25 | | |

| AAC | AGU | CAA | AAC | CAA | AGU | AAC | AAC | CAG | UUU | GUA | UUG | UAC | 117 |
| Asn | Ser | Gln | Asn | Gln | Ser | Asn | Asn | Gln | Phe | Val | Leu | Tyr | |

-continued
Sequence Description: Seq Id No: 1:

| | | | | | | | | | | | | | |
|---|---|---|---|---|---|---|---|---|---|---|---|---|---|
| | | | | | 30 | | | | 35 | | | | |
| CGC Arg 40 | AUA Ile | ACU Thr | GAA Glu | GCC Ala | ACU Thr 45 | AAG Lys | ACG Thr | GUU Val | GGC Gly | UCU Ser 50 | GAC Asp | ACG Thr | 156 |
| UUU Phe | UAU Tyr | UCC Ser 55 | UUC Phe | AAG Lys | UAC Tyr | GAA Glu | AUC Ile 60 | AAG Lys | GAG Glu | GGG Gly | GAU Asp | UGU Cys 65 | 195 |
| CCU Pro | GUU Val | CAA Gln | AGU Ser | GGC Gly 70 | AAA Lys | ACC Thr | UGG Trp | CAG Gln | GAC Asp 75 | UGU Cys | GAG Glu | UAC Tyr | 234 |
| AAG Lys | GAU Asp 80 | GCU Ala | GCA Ala | AAA Lys | GCA Ala 85 | GCC Ala | ACU Thr | GGA Gly | GAA Glu | UGC Cys | ACG Thr 90 | GCA Ala | 273 |
| ACC Thr | GUG Val | GGG Gly | AAG Lys 95 | AGG Arg | AGC Ser | AGU Ser | ACG Thr | AAA Lys 100 | UUC Phe | UCC Ser | GUG Val | GCU Ala | 312 |
| ACC Thr 105 | CAG Gln | ACC Thr | UGC Cys | CAG Gln | AUU Ile 110 | ACU Thr | CCA Pro | GCC Ala | GAG Glu | GGC Gly 115 | CCU Pro | GUG Val | 351 |
| GUG Val | ACA Thr | GCC Ala 120 | CAG Gln | UAC Tyr | GAC Asp | UGC Cys | CUC Leu 125 | GGC Gly | UGU Cys | GUG Val | CAU His | CCU Pro 130 | 390 |
| AUA Ile | UCA Ser | ACG Thr | CAG Gln | AGC Ser 135 | CCA Pro | GAC Asp | CUG Leu | GAG Glu | CCC Pro 140 | AUU Ile | CUG Leu | AGA Arg | 429 |
| CAC His | GGC Gly 145 | AUU Ile | CAG Gln | UAC Tyr | UUU Phe | AAC Asn 150 | AAC Asn | AAC Asn | ACU Thr | CAA Gln | CAU His 155 | UCC Ser | 468 |
| UCC Ser | CUC Leu | UUC Phe | AUG Met 160 | CUU Leu | AAU Asn | GAA Glu | GUA Val | AAA Lys 165 | CGG Arg | GCC Ala | CAA Gln | AGA Arg | 507 |
| CAG Gln 170 | GUG Val | GUG Val | GCU Ala | GGA Gly | UUG Leu 175 | AAC Asn | UUU Phe | CGA Arg | AUU Ile | ACC Thr 180 | UAC Tyr | UCA Ser | 546 |
| AUU Ile | GUG Val | CAA Gln 185 | ACG Thr | AAU Asn | UGU Cys | UCC Ser | AAA Lys 190 | GAG Glu | AAU Asn | UUU Phe | CUG Leu | UUC Phe 195 | 585 |
| UUA Leu | ACU Thr | CCA Pro | GAC Asp | UGC Cys 200 | AAG Lys | UCC Ser | CUU Leu | UGG Trp | AAU Asn 205 | GGU Gly | GAU Asp | ACC Thr | 624 |
| GGU Gly | GAA Glu 210 | UGU Cys | ACA Thr | GAU Asp | AAU Asn | GCA Ala 215 | UAC Tyr | AUC Ile | GAU Asp | AUU Ile | CAG Gln 220 | CUA Leu | 663 |
| CGA Arg | AUU Ile | GCU Ala | UCC Ser 225 | UUC Phe | UCA Ser | CAG Gln | AAC Asn | UGU Cys 230 | GAC Asp | AUU Ile | UAU Tyr | CCA Pro | 702 |
| GGG Gly 235 | AAG Lys | GAU Asp | UUU Phe | GUA Val | CAA Gln 240 | CCA Pro | CCU Pro | ACC Thr | AAG Lys | AUU Ile 245 | UGC Cys | GUG Val | 741 |
| GGC Gly | UGC Cys | CCC Pro 250 | AGA Arg | GAU Asp | AUA Ile | CCC Pro | ACC Thr 255 | AAC Asn | AGC Ser | CCA Pro | GAG Glu | CUG Leu 260 | 780 |
| GAG Glu | GAG Glu | ACA Thr | CUG Leu | ACU Thr 265 | CAC His | ACC Thr | AUC Ile | ACA Thr | AAG Lys 270 | CUU Leu | AAU Asn | GCA Ala | 819 |
| GAG Glu | AAU Asn 275 | AAC Asn | GCA Ala | ACU Thr | UUC Phe | UAU Tyr 280 | UUC Phe | AAG Lys | AUU Ile | GAC Asp | AAU Asn 285 | GUG Val | 858 |
| AAA Lys | AAA Lys | GCA Ala | AGA Arg 290 | GUA Val | CAG Gln | GUG Val | GUG Val | GCU Ala 295 | GGC Gly | AAG Lys | AAA Lys | UAU Tyr | 897 |

-continued
Sequence Description: Seq Id No: 1:

| | | | | | | | | | | | | | |
|---|---|---|---|---|---|---|---|---|---|---|---|---|---|
| UUU Phe 300 | AUU Ile | GAC Asp | UUC Phe | GUG Val | GCC Ala 305 | AGG Arg | GAA Glu | ACC Thr | ACA Thr | UGU Cys 310 | UCC Ser | AAG Lys | 936 |
| GAA Glu | AGU Ser | AAU Asn 315 | GAA Glu | GAG Glu | UUG Leu | ACC Thr | GAA Glu 320 | AGC Ser | UGU Cys | GAG Glu | ACC Thr | AAA Lys 325 | 975 |
| AAA Lys | CUU Leu | GGC Gly | CAA Gln | AGC Ser 330 | CUA Leu | GAU Asp | UGC Cys | AAC Asn | GCU Ala 335 | GAA Glu | GUU Val | UAU Tyr | 1014 |
| GUG Val | GUA Val 340 | CCC Pro | UGG Trp | GAG Glu | AAA Lys | AAA Lys 345 | AUU Ile | UAC Tyr | CCU Pro | ACU Thr | GUC Val 350 | AAC Asn | 1053 |
| UGU Cys | CAA Gln | CCA Pro | CUG Leu 355 | GGA Gly | AUG Met | AUC Ile | UCA Ser | CUG Leu 360 | AUG Met | AAA Lys | AGG Arg | CCU Pro | 1092 |
| CCA Pro 365 | GGU Gly | UUU Phe | UCA Ser | CCU Pro | UUC Phe 370 | CGA Arg | UCA Ser | UCA Ser | CGA Arg | AUA Ile 375 | GGG Gly | GAA Glu | 31131 |
| AUA Ile | AAA Lys | GAA Glu 380 | GAA Glu | ACA Thr | ACU Thr | GUA Val | AGU Ser 385 | CCA Pro | CCC Pro | CAC His | ACU Thr | UCC Ser 390 | 1170 |
| AUG Met | GCA Ala | CCU Pro | GCA Ala | CAA Gln 395 | GAU Asp | GAA Glu | GAG Glu | CGG Arg | GAU Asp 400 | UCA Ser | GGA Gly | AAA Lys | 1209 |
| GAA Glu | CAA Gln 405 | GGG Gly | CAU His | ACU Thr | CGU Arg | AGA Arg 410 | CAU His | GAC Asp | UGG Trp | GGC Gly | CAU His 415 | GAA Glu | 1248 |
| AAA Lys | CAA Gln | AGA Arg | AAA Lys 420 | CAU His | AAU Asn | CUU Leu | GGC Gly | CAU His 425 | GGC Gly | CAU His | AAA Lys | CAU His | 1287 |
| GAA Glu 430 | CGU Arg | GAC Asp | CAA Gln | GGG Gly | CAU His 435 | GGG Gly | CAC His | CAA Gln | AGA Arg | GGA Gly 440 | CAU His | GGC Gly | 1326 |
| CUU Leu | GGC Gly | CAU His 445 | GGA Gly | CAC His | GAA Glu | CAA Gln | CAG Gln 450 | CAU His | GGU Gly | CUU Leu | GGU Gly | CAU His 455 | 1365 |
| GGA Gly | CAU His | AAG Lys | UUC Phe | AAA Lys 460 | CUU Leu | GAU Asp | GAU Asp | GAU Asp | CUU Leu 465 | GAA Glu | CAC His | CAA Gln | 1404 |
| GGG Gly | GGC Gly 470 | CAU His | GUC Val | CUU Leu | GAC Asp | CAU His 475 | GGA Gly | CAU His | AAG Lys | CAU His | AAG Lys 480 | CAU His | 1443 |
| GGU Gly | CAU His | GGC Gly | CAC His 485 | GGA Gly | AAA Lys | CAU His | AAA Lys | AAU Asn 490 | AAA Lys | GGC Gly | AAA Lys | AAG Lys | 1482 |
| AAU Asn 495 | GGA Gly | AAG Lys | CAC His | AAU Asn | GGU Gly 500 | UGG Trp | AAA Lys | ACA Thr | GAG Glu | CAU His 505 | UUG Leu | GCA Ala | 1521 |
| AGC Ser | UCU Ser | UCU Ser 510 | GAA Glu | GAC Asp | AGU Ser | ACU Thr | ACA Thr 515 | CCU Pro | UCU Ser | GCA Ala | CAG Gln | ACA Thr 520 | 1560 |
| CAA Gln | GAG Glu | AAG Lys | ACA Thr | GAA Glu 525 | GGG Gly | CCA Pro | ACA Thr | CCC Pro | AUC Ile 530 | CCU Pro | UCC Ser | CUA Leu | 1399 |
| GCC Ala | AAG Lys 535 | CCA Pro | GGU Gly | GUA Val | ACA Thr | GUU Val 540 | ACC Thr | UUU Phe | UCU Ser | GAC Asp | UUU Phe 545 | CAG Gln | 1638 |
| GAC Asp | UCU Ser | GAU Asp | CUC Leu 550 | AUU Ile | GCA Ala | ACU Thr | AUG Met | AUG Met 555 | CCU Pro | CCU Pro | AUA Ile | UCA Ser | 1677 |
| CCA Pro | GCU Ala | CCC Pro | AUA Ile | CAG Gln | AGU Ser | GAU Asp | GAC Asp | GAU Asp | UGG Trp | AUC Ile | CCU Pro | GAU Asp | 1716 |

-continued
Sequence Description: Seq Id No: 1:

| Pro 560 | Ala | Pro | Ile | Gln | Ser 565 | Asp | Asp | Asp | Trp | Ile 570 | Pro | Asp | |
|---|---|---|---|---|---|---|---|---|---|---|---|---|---|
| AUC Ile | CAG Gln | AUA Ile 575 | GAC Asp | CCA Pro | AAU Asn | GGC Gly | CUU Leu 580 | UCA Ser | UUU Phe | AAC Asn | CCA Pro | AUA Ile 585 | 1755 |
| UCA Ser | GAU Asp | UUU Phe | CCA Pro | GAC Asp 590 | ACG Thr | ACC Thr | UCC Ser | CCA Pro | AAA Lys 595 | UGU Cys | CCU Pro | GGA Gly | 1794 |
| CGC Arg | CCC Pro 600 | UGG Trp | AAG Lys | UCA Ser | GUU Val | AGU Ser 605 | GAA Glu | AUU Ile | AAU Asn | CCA Pro | ACC Thr 610 | ACA Thr | 1833 |
| CAA Gln | AUG Met | AAA Lys | GAA Glu 615 | UCU Ser | UAU Tyr | UAU Tyr | UUC Phe | GAU Asp 620 | CUC Leu | ACU Thr | GAU Asp | GGC Gly | 1872 |
| CUU Leu 625 | UCU Ser | -3' | | | | | | | | | | | 1911 |

We claim:

1. A method for reducing the tendency of a composition selected from the group of a blood component and an animal cell, to adhere a surface, the method comprising coating the surface with an exogenously supplied proteinaceous material that is present in passifin, whereby the tendency of said composition to adhere to the surface is reduced.

2. The method of claim 1, wherein the material has histidine in it.

3. The method of claim 2, wherein the material is two chain molecules connected with a disulfide bond.

4. The method of claim 3, wherein the material does not have a kinin portion.

5. The method of claim 1, wherein the surface is plastic.

6. The method of claim 1, wherein the surface is on the interior of conduit.

7. A surface made of a substance that has been produced outside of an animal, the surface then having been at least partially coated with a proteinaceous material present in passifin.

* * * * *